United States Patent [19]

Saito et al.

[11] Patent Number: 5,103,064
[45] Date of Patent: Apr. 7, 1992

[54] PROCESS FOR PRODUCING A CARBONYL COMPOUND

[75] Inventors: Yoshinori Saito; Masanori Tsuzuki, both of Sodegaura, Japan

[73] Assignee: Idemitsu Kosan Company Limited, Tokyo, Japan

[21] Appl. No.: 578,591

[22] Filed: Sep. 4, 1990

[30] Foreign Application Priority Data

Sep. 19, 1989 [JP] Japan .................................. 1-243065

[51] Int. Cl.$^5$ ............................................ C07C 45/34
[52] U.S. Cl. .................................... 568/401; 568/478
[58] Field of Search ........................ 568/401, 475, 478

[56] References Cited

U.S. PATENT DOCUMENTS

| | | | |
|---|---|---|---|
| 4,271,320 | 6/1981 | Tokitoh et al. | 568/475 |
| 4,507,506 | 3/1985 | Shioyama | 568/401 |
| 4,507,507 | 3/1985 | Murtha | 568/401 |
| 4,521,631 | 6/1985 | Nishimura et al. | 568/478 |
| 4,661,642 | 4/1987 | Feringa | 568/475 |
| 4,723,041 | 2/1988 | Vasilevskis et al. | 568/401 |

*Primary Examiner*—James H. Reamer
*Attorney, Agent, or Firm*—Frishauf, Holtz, Goodman & Woodward

[57] ABSTRACT

A carbonyl compound is produced efficiently, stably and with good productivity by oxidizing a chain olefin in an alcoholic solvent in the presence of a catalyst system comprising palladium and a polyoxoanion as active components.

40 Claims, No Drawings

PROCESS FOR PRODUCING A CARBONYL COMPOUND

BACKGROUND OF THE INVENTION

1. Field of the Invention

The present invention relates to a process for producing a carbonyl compound. More particularly, it relates to a process for producing efficiently and stably various carbonyl compounds useful as solvents, chemical raw materials and the like, by catalytic oxidation of a chain olefin.

2. Description of Prior Art

The carbonyl compounds, e.g. ketones such as methylethylketone, methylisobutylketone, acetone, etc. and aldehydes such as acetaldehyde, etc. are useful as solvents, chemical raw materials and the like. Most of such carbonyl compounds are usually produced in two-steps by hydrating an olefin followed by dehydrogenating the resultant alcohol. It has been desired to produce these carbonyl compounds in one-step by oxidizing an olefin directly.

As a process for producing a carbonyl compound by the direct oxidation of an olefin, the Wacker process using a $PdCl_2$—$CuCl_2$ catalyst has been known since long ago. This process, however, has not been utilized except for the production of a lower carbonyl compound such as acetaldehyde, acetone, etc., because the reaction rate remarkably goes down, as the carbon number of an olefin increases. In addition, problems such as corrosion of the process equipment and generation of by-products including chlorine-containing compounds have been encountered in the Wacker process, because it needs to use a relatively large amount of active chlorine compounds.

Recently, other several direct olefin oxidation methods have been suggested in order to solve these problems.

For example, Japanese laid-open patent application No. 117189/76 discloses a method using a palladium compound and a heteropolyacid or an isopolyacid as a catalyst.

This method, however, needs a relatively large amount of the catalyst due to the poor activity thereof and also requires a large excess amount of the heteropolyacid or the isopolyacid to the palladium compound. This leads to poor reaction efficiency and also causes corrosion of the equipment. In this method there are further problems that isomerization of an olefin is likely to occur and selectivity (e.g. selectivity from 1-hexene to 2-hexanone) decreases.

Further, U.S. Pat. No. 4,550,212 discloses a method using a Pd-heteropolyacid type catalyst to which $H_3BO_3$, acetyltrimethylammonium bromide (surfactant) and the like are added, wherein the reaction is performed in a two-phase solvent of decane and water.

This method, however, also includes problems that the reactivity (TON, i.e. turnover number) is low and the recovery of the desired products, catalyst components, etc. is troublesome.

Moreover, Japanese laid-open patent application No. 500923/88 proposes a method which uses a catalyst system made by adding a redox-metal such as Cu, Fe, Mn, etc. and/or a ligand (acetonitrile, etc.) to the Pd-heteropolyacid.

In this method, however, the initial reaction rate is high, but as the reaction proceeds, the precipitation of catalyst components takes place, resulting in the inconvenience of operation and the lower reaction rate. As the result, the reactivity (TON) and productivity are undesirably lowered.

SUMMARY OF THE INVENTION

An object of the present invention is to provide a remarkably practical and useful process for producing a carbonyl compound, which process has advantages that, in the catalytic oxidation of a chain olefin with a catalyst system comprising palladium and a polyoxoanion as active components, (i) the reactivity of the chain olefin to a carbonyl compound such as a ketone and an aldehyde can be improved and (ii) the precipitation of the catalyst components can be prevented, thereby maintaining the substantial catalyst activity stably at an elevated level, and as a result, (iii) a carbonyl compound can be produced at a high efficency and productivity.

The other objects of the present invention will be apparent from the following description.

The above mentioned objects of the present invention can be achieved by a process for producing a carbonyl compound, which comprises oxidizing a chain olefin in an alcoholic solvent in the presence of a catalyst system comprising palladium and a polyoxoanion as active components.

Accordingly, the present invention resides in a process for producing a carbonyl compound, which comprises oxidizing a chain olefin in an alcoholic solvent in the presence of a catalyst system comprising palladium and a polyoxoanion as active components.

DETAILED DESCRIPTION OF THE INVENTION

Hereunder, the present invention is described in detail.

According to the present invention, a catalyst system comprising palladium and a polyoxoanion as active components is used as a catalyst. The catalyst system is generally composed of a palladium compound and a polyoxoanion compound.

There is no limitation to the palladium compound mentioned above, provided that it contains palladium (Pd) as a metal component. Concretely, it includes, for example, palladium sulfate; palladium nitrate; palladium-containing polyoxoanion compounds such as a palladium salt of a heteropolyacid, a palladium salt of an isopolyacid, etc.; inorganic palladium salts such as halogenides, e.g. palladium chloride, palladium bromide, etc.; organic palladium salts such as palladium acetate, etc.; palladium hydroxide; palladium oxide; and the like. The palladium compound includes organic or inorganic complexes such as. ammine complexes or amine complexes with the above compounds, halogeno complexes with the above compounds (including e.g. complex salts such as tetrachloropalladium acid, a sodium salt thereof or a potassium salt thereof), organic palladium compounds, and the like. Among these, palladium sulfate and the like are particularly preferable.

These palladium compounds may be employed alone or as a mixture or a conjugated compound of two or more palladium compounds mentioned above. These palladium compounds may be anhydrous or hydrous.

There is no particular limitation to the polyoxoanion compound used in the present invention, provided that it contains a polyoxoanion. The suitable polyoxoanion compound possesses enough oxidation potential to Pd (re-oxidation potential to Pd in a catalytic cycle) and is such compound that a reduced-type polyoxoanion formed after re-oxidation of Pd can be easily re-oxidized by oxidizing agents such as oxygen and the like.

The polyoxoanion mentioned above may be either a heteropolyoxoanion or an isopolyoxoanion.

The heteropolyoxoanion used in the present invention contains heteroatom(s) such as P, Si, As, Ge, B, Se, Te and the like. The suitable heteropoloyoxoanion is one including P or Si (especially P) as a heteroatom.

Further, the heteropolyoxoanion and isopolyoxoanion include a single metal component type containing one of Mo, W, V, Nb, Ta, etc., and a mixed coordination type containing at least two atoms as above. Both types may be used but the mixed coordination type including Mo, W, V and the like is preferable. As the above single metal component type, the heteropolyoxoanion and isopolyoxoanion containing Mo or V are preferable.

As the mixed coordination type, the heteropolyoxoanion and isopolyoxoanion having Mo and V; W and V; or Mo, V and W are especially preferable.

Examples of the heteropolyoxoanion mentioned above may include:
$[PMo_6 V_6 O_{40}]^{9-}$, $[PMo_4 V_8 O_{40}]^{11-}$,
$[PMo_8 V_4 O_{40}]^{7-}$ $[P_2 W_{12}Mo_5 VO_{62}]^{7-}$,
$[P_2 W_{15}Mo_2 VO_{62}]^{7-}$ and the like.

Examples of the isopolyoxoanion mentioned above may include:
$[Mo_4 V_8 O_{38}]^{8-}$, $[Mo_3 V_3 3O_{19}]^{5-}$,
$[Mo_6 V_2 O_{26}]^{6-}$, $[Mo_6 V_6 O_{36}]^{6-}$,
$[W_7 Mo_3 V_2 O_{36}]^{2-}$, $[Mo_8 V_4 O_{36}]^{4-}$ and the like.

The above polyoxoanion compound may include compounds consisting of the above heteropolyoxoanion or the above isopolyoxoanion and one or more cation components (counter cation), i.e. heteropolyacids or salts thereof and isopolyacids or salts thereof.

Among these, the heteropolyacids and salts thereof are suitable in light of their activity and the like.

Among the polyoxoanion compound described above, there are preferable the heteropolyacids or salts thereof having the heteropolyoxoanion of the mixed coordination type containing Mo, W, V, etc. as metal components. More concretely, following the compounds or salts thereof are preferable.
$H_9 [PMo_6 V_6 O_{40}]$, $H_{11}[PMo_4 V_8 O_{40}]$,
$H_7 [PMo_8 V_4 O_{40}]$, $H_7 [P_2 W_{12}Mo_5 VO_{62}]$,
$H_7 [P_2 W_{15}Mo_2 VO_{62}]$, and the like.

Further, salts of the above heteropolyacids and salts of the above isopolyacids may be partial salts where $H^+$ remains partially, and normal salts of the completely neutralized type.

There is no specific limitation to the above cation components. They may include $H^+$, various metallic cations (e.g. alkali metal ions such as $Li^+$, $Na^+$ $K^+$ etc., alkaline earth metal ions such as $Ca^{2+}$ $Mg^{2+}$, etc., transition metal ions such as $Cu^{2+}$, $Pd^{2+}$, $Fe^{2+}$, $Mn^{2+}$, $Co^{2+}$, etc., or metal complex ions thereof) and nonmetallic cations such as onium ions, e.g., ammonium ion (including secondary, tertiary or quarternary ammonium ions), and the like. Usually, the object of the present invention may be fully achieved when the cation component is $H^+$. That is, usually, the polyoxoanion compound (heteropolyacids or isopolyacids) of the $H^+$ type are preferably used in the present invention.

Further, the various polyoxoanion compounds described above may contain crystallization water.

The polyoxoanion compound mentioned above may be used alone or as a mixture or a complex of two or more thereof.

The catalyst system for use in the present invention may be formed by mixing an above palladium compound and an above polyoxoanion compound.

When palladium salts of the heteropolyacid or palladium salts of the isopolyacid are selected, they may be used as the palladium compound or as the polyoxoanion compound.

A ratio of the polyoxoanion compound to the palladium compound is determined in such a manner that an amount of the polyoxoanion compound ranges usually from 0.5 to 100 moles, preferably from 1 to 20 moles per 1 mole of the palladium compound.

In case that the amount of the polyoxoanion compound is less than 0.5 mole, re-oxidation of Pd in the catalytic cycle does not proceed satisfactorily and the elevated level of activity may not be obtained. On the contrary, when it is more than 100 moles, undesired by-products are likely to be formed.

As mentioned above, the catalyst system used in the present invention may include palladium and a polyoxoanion as catalyst components. Therefore when a compound containing both palladium and a polyoxoanion in the molecule, such as palladium salts of the heteropolyacid or of the isopolyacid is selected, the catalyst system can be composed with this compound only.

The catalyst system mentioned above may contain other co-catalyst components (including a ligand component), if desired, to extent that does not impair the object of the present invention.

One of the important aspects in the present invention resides in that the oxidation of a chain olefin with the above catalyst system is performed in an alcoholic solvent to produce a carbonyl compound.

Examples of alcohol used in the above solvent include, monohydric alcohols having 1 to 7 carbon atoms such as methanol, ethanol, n-propanol, isopropanol, n-butanol, sec-butanol, n-pentanol, n-hexanol, etc. and polyhydric alcohols having 1 to 7 carbon atoms such as ethylene glycol, propylene glycol, etc.

Among these, alcohols having 1 to 4 carbon atoms such as methanol, ethanol, ethylene glycol, etc. are preferable.

The alcohol mentioned above may be used alone or as mixed solvent of two or more thereof.

The solvent mentioned above contains an alcohol and may also contain water unless imparing the object of the invention. A far larger amount of water to the alcohol results in the substantial decrease of olefin solubility and reduced reaction efficiency, thereby causing the precipitation of Pd during the reaction. Accordingly, the less proportion of water is preferable, and generally not more than 60% by weight. The suitable proportion of water contained in the solvent is not more than 40%, especially not more than 15% by weight.

Further, the solvent mentioned above may contain other solvents unless imparing the object of the invention.

The solvent mentioned above is employed in an amount enough to solve the catalyst system used. Generally about 1 to 10,000 liters of the solvent per one mole of the palladium compound is used.

The chain olefin used as a reactant material in the present invention has a double bond (C=C) at any of the terminal or the internal thereof and may be in any form of trans- or cis-type.

There is no limitation to the olefin mentioned above, provided that the carbon number thereof is two or more. Generally the carbon number is from 2 to 20, preferably from 2 to 8.

The chain olefin may be straight or branched.

Examples of the chain olefin mentioned above include, for example, ethylene, propylene, 1-butene, trans-2-butene, cis-2-butene, isobutene, 1-penten, 2-penten, isopentene (e.g. 3-methyl-1-butene), 1-hexene, 2-hexene, 3-hexene, isohexene (e.g. 3-methyl-1-pentene, 4-methyl-1-pentene, 4-methyl-2-penten), neohexene, 1-heptene, 2-heptene, isoheptene (e.g. 4-methyl-1-hexene), 1-octene, 2-octene, 3-octene, 4-octene, isooctene, (e.g. 5-methyl-1-heptene), 1-nonene, 2-nonene, isononene (e.g. 6-methyl-1-octene), 1-decene, 2-decene, 3-decene, 4-decene, 5-decene, isodecene (e.g. 7-methyl-1-nonene), undecene, dodecene, tridecene, tetradecene, hexadecene.

Among these, suitable olefins are ethylene, propylene, 1-butene, trans-2-butene, cis-2-butene, 1-pentene, 2-pentene, 1-hexene, 2-hexene, 3-hexene, 4-methyl-1-pentene, 1-heptene, 1-octene, etc.

The chain olefin may be employed alone or as a mixture of two or more thereof.

Further, the reactant material may contain other components unless imparing the object of the present invention.

The ratio of the olefin mentioned above to the catalyst system may depend on the activity of the catalyst system and other reaction conditions and hence can not be generally determined. Usually, the molar ratio of the olefin to the palladium compound is from 10 to 2,000, preferably from 50 to 1,000.

A far less ratio leads to decreased productivity per catalyst and causes economical disadvantage, whereas if the ratio is too large, satisfactory conversion may not be obtained or the reaction may take a longer time.

When the reaction is carried out in a continuous process where the chain olefin is continuously supplied, a suitable gaseous hourly space velocity (GHSV) is generally in a range of 20 to 1,000 per hour.

As an oxidizing agent used in the oxidation of the chain olefin mentioned above, pure oxygen or a mixed gas of oxygen with a diluent gas may preferably be used. An example of the mixed gas is air.

There is no particular limitation to the reaction method. Although a batch method, a continuous process or a semi-continuous process where only the oxidizing agent is flowed may be employed, usually the batch method under elevated pressure or autopressure as well as the continuous process where the reactant is flowed into the catalyst solution under atmospheric pressure or elevated pressure may suitably be employed.

The suitable reaction temperature is usually in a range of 0° to 200° C., more suitably of 20° to 100° C.

At a temperature of less than 0° C., the reaction rate becomes slow, whereas at a temperature of over 200° C., side reactions may be likely to occur.

The reaction pressure may be selected from a wide range of atmospheric pressure to elevated pressure, and generally the pressure ranging from atmospheric pressure to 20 Kg/cm$^2$ is economically preferable.

In accordance with the process described above, a carbonyl compound such as aldehydes and ketones or mixtures thereof may be efficiently and stably obtained from the corresponding chain olefin.

For example, when ethylene is employed as a chain olefin, acetaldehyde is obtained; when propylene is utilized, acetone is produced; and methylethylketone is mainly obtained from 1-butene, 2-butene or the mixture thereof. Methylisobutylketone is produced from 4-methyl-1-pentene.

The carbonyl compound thus obtained is isolated and purified in a conventional manner, and recovered as a single compound with desired purity or a mixture with desired composition. Unreacted residual reactant materials, if any, may be recovered and then recycled into the reaction system. The catalyst or catalytic components used may be regenerated or separated, if necessary, and may be employed repeatedly.

The various carbonyl compounds thus prepared may conveniently be utilized, for example, as solvents, chemicals, etc. in various fields such as synthetic chemistry.

The following Examples and Comparative Examples illustrate further concretely the present invention.

The present invention is not limited to the following Examples and may include various modified embodiments, unless the gist of the invention is altered.

EXAMPLE 1

A solution of 0.4 mmol (0.0954 g) of PdSO$_4$.2H$_2$O and 1.8 mmol (3.8807 g, water content 23.7% by weight) of H$_7$[PMo$_8$V$_4$O$_{40}$] in 30 ml of absolute methanol was charged to an autoclave and 200 mmol (11.2 g) of trans-2-butene and oxygen were reacted for 2 hours at 50° C. under a pressure of 7 Kg/cm$^2$ (absolute pressure, maintained by oxygen supply).

As a result, 149.3 mmol (10.7 g) of methylethylketone (MEK) was produced and TON (turnover number) based upon Pd was 187. No deposit was recovered from the reaction solution.

"TON" used herein represents an amount (mol) of the resultant MEK per unit hour (hr) and per unit Pd (mol).

EXAMPLES 2-5

The reaction was performed in a manner similar to Example 1 with the exception that ethanol, n-propanol, n-butanol and ethylene glycol were employed in place of methanol.

The results are indicated in Table 1.

EXAMPLES 6 AND 7

The reaction was carried out in a manner similar to Example 1 with the exception that a mixture of 15 ml ethanol and 15 ml water or a mixture of 22.5 ml ethanol and 7.5 ml water was used in place of 30 ml methanol.

The results are shown in Table 1.

EXAMPLE 8

The reaction was effected in a manner similar to Example 1 with the exception that ethanol was used in place of methanol, and reaction temperature, pressure and time were 90° C., 10 Kg/cm$^2$ (absolute pressure) and 0.5 hour, respectively.

The result is shown in Table 1.

COMPARATIVE EXAMPLE 1

The reaction was conducted in a manner similar to Example 1 with the exception that 30 ml water was used in place of 30 ml methanol.

The result is indicated in Table 1.

COMPARATIVE EXAMPLE 2

The reaction was performed in a manner similar to Example 1 with the exception that 30 ml water was used in place of 30 ml methanol, and further 2.0 mmol (0.4999 g) of $CuSO_4 \cdot 5H_2O$ and 10 ml of acetonitrile were added.

The result is shown in Table 1.

TABLE 1

| Example No. | solvent | amount of MEK formed [mmol] | TON $\left[\frac{mol\text{-}MEK}{mol\text{-}Pd \cdot hr}\right]$ | amount of deposit recovered [g] |
|---|---|---|---|---|
| Example 1 | methanol[b] | 149.3 | 187 | none |
| Example 2 | ethanol[a] | 116.1 | 145 | none |
| Example 3 | n-propanol[b] | 62.8 | 79 | none |
| Example 4 | n-butanol[b] | 78.7 | 98 | none |
| Example 5 | ethylene glycol[b] | 71.2 | 89 | none |
| Example 6 | ethanol[c] | 34 | 43 | none |
| Example 7 | ethanol[d] | 46 | 57 | none |
| Example 8 | ethanol[a] | 87.7 | 439 | none |
| Comparative Example 1 | water | 1.6 | 1 | 0.0872 |
| Comparative Example 2 | water and acetonitrile | 50.7 | 63 | 0.0838 |

Remarks
[a] water content 0.5% by weight
[b] absolute
[c] water content 56.4% by weight
[d] water content 30.3% by weight

EXAMPLE 9

A solution of 1.0 mmol (0.2385 g) of $PdSO_4.2H_2O$ and 1.0 mmol (2.2 g, water content 23.7% by weight) of $H_7[PMo_8 V_4 O_{40}]$ in 60 ml of ethanol (water content 0.5% by weight) was charged to a reactor, into which 43 ml/min of 1-butene and 19 ml/min of oxygen were blown, and then they were reacted for 2 hours under reflux.

As a result, 15.6 mmol (1.12 g) of methylethylketone (MEK) was produced.

EXAMPLE 10

The reaction was carried out in a manner similar to Example 9 with the exception that sec-butanol was employed in place of ethanol. As a result, 18.2 mmol (1.31 g) of MEK was produced and no deposit was recovered from the reaction solution.

EXAMPLE 11

The reaction was carried out at 50° C. in a manner similar to Example 9 except for using propylene in place of 1-butene.

As a result, 75.1 mmol (4.36 g) of acetone was formed.

EXAMPLE 12

The reaction was performed at 50° C. in a manner similar to Example 9 with the exception that n-propanol and ethylene were used in place of ethanol and 1-butene, respectively.

As a result, 73.1 mmol (3.21 g) of acetaldehyde was formed.

In accordance with the present invention, the reactivity (TON) of a chain olefin into a carbonyl compound such as ketones and aldehydes can be remarkably increased, and the precipitation of catalyst components can be prevented efficiently so that activity of the catalyst can be stably maintained at an elevated level not only at an initial stage of the reaction but also for long time.

Accordingly the present invention can provide a process in which useful carbonyl compounds can be produced efficiently, stably and with good productivity.

What is claimed is:

1. A process for producing a carbonyl compound which comprises oxidizing a straight or branched chain olefin having 2 to 20 carbon atoms in an alcoholic solvent comprising a monohydric primary or secondary alcohol having 1 to 7 carbon atoms, a polyhydric alcohol having 1 to 7 carbon atoms or a mixture of said monohydric and polyhydric alcohols in the presence of a catalyst system consisting essentially of palladium and a polyoxoanion as active components, said polyoxoanion being selected from the group consisting of a heteropolyoxoanion and an isopolyoxoanion, both of which heteropolyoxoanion and isopolyoxoanion comprise a single metal component selected from the group consisting of Mo, W, V, Nb and Ta or a mixed coordination component comprising at least two metals selected from the group consisting of Mo, W, V, Nb and Ta, the oxidation being carried out in the presence of an oxidizing agent selected from the group consisting of pure oxygen and a mixed gas of oxygen with a diluent gas and at a temperature of 0° to 200° C. and at a pressure of atmospheric pressure to 20 kg/cm$^2$.

2. The process according to claim 1, wherein the solvent is a monohydric alcohol selected from the group consisting of methanol, ethanol, n-propanol, isopropanol, n-butanol, sec-butanol, n-pentanol and n-hexanol.

3. The process according to claim 1, wherein the alcoholic solvent comprises an alcohol having 1 to 7 carbon atoms.

4. The process according to claim 1, wherein the solvent is a polyhydric alcohol selected from the group consisting of ethylene glycol and propylene glycol.

5. The process according to claim 1, wherein the alcoholic solvent further comprises water.

6. The process according to claim 5, wherein an amount of water contained in the alcoholic solvent is not more than 60% by weight.

7. The process according to claim 6, wherein an amount of water contained in the alcoholic solvent is not more than 40% by weight.

8. The process according to claim 1, wherein the catalyst system is comprises a single compound which contains both palladium and a poly oxoanion in the molecule.

9. The process according to claim 1, wherein the olefin has 2 to 8 carbon atoms.

10. The process according to claim 1, wherein the olefin has 2 to 4 carbon atoms.

11. The process according to claim 1, wherein the palladium is in the form of a palladium compound selected from the group consisting of palladium sulfate, palladium nitrate, palladium chloride, palladium bromide, palladium acetate, palladium hydroxide, palladium oxide and tetrachloropalladium acid.

12. The process according to claim 11, wherein the polyoxoanion is in the form of a compound with a counter cation, the polyoxoanion being selected from the group consisting of
$(PMo_6 V_6 O_{40})^{9-}$, $(PMo_4 V_8 O_{40})^{11-}$,
$(PMo_8 V_4 O_{40})^{7-}$, $(P_2 W_{12}Mo_5 VO_{62})^{7-}$,
$(P_2 W_{15}Mo_2 VO_{62})^{7-}$,
$(Mo_4 V_8 O_{38})^{8-}$, $(Mo_3 V_3 3O_{19})^{5-}$,
$(Mo_6 V_2 O_{26})^{6-}$, $(Mo_6 V_6 O_{36})^{6-}$,
$(W_7 Mo_3 V_2 O_{36})^{2-}$ and
$(Mo_8 V_4 O_{36})^{4-}$
and the counter cation being selected from the group consisting of $H^+$, $Li^+$, $Na^+$, $K^+$, $Ca^{2+}$, $Mg^{2+}$, $Co^{2+}$, $Pd^{2+}$, $Fe^{2+}$, $Mn^{2+}$, $Co^{2+}$, onium and ammonium.

13. The process according to claim 12, wherein the polyoxoanion compound is selected from the group consisting of
$H_9 (PMo_6 V_6 O_{40})$, $H_{11}(PMo_4 V_8 O_{40})$,
$H_7 (PMo_8 V_4 O_{40})$, $H_7 (P_2 W_{12}Mo_5 VO_{62})$ and
$H_7 (P_2 W_{15}Mo_2 VO_{62})$.

14. The process according to claim 13, wherein the polyoxoanion is in an amount of 1 to 20 moles per mole of the palladium.

15. The process according to claim 14, wherein the solvent consists essentially of an alcohol selected from the group consisting of methanol, ethanol, n-propanol, isopropanol, n-butanol, sec-butanol, n-pentanol, n-hexanol, ethylene glycol and propylene glycol.

16. The process according to claim 15, wherein the alcohol is in an amount of 1 to 10,000 liters per mole of the palladium.

17. The process according to claim 16, wherein the olefin is selected from the group consisting of ethylene, propylene, 1-butene, trans-2-butene, cis-2-butene, 1-pentene, 2-pentene, 1-hexene, 2-hexene, 3-hexene, 4-methyl-1-pentene, 1-heptene and 1-octene and the olefin is in an amount of 10 to 2,000 moles olefin per mole of the palladium.

18. The process according to claim 17, wherein the oxidizing is carried out at a gaseous hourly space velocity of 20 to 1,000 per hour.

19. The process according to claim 18, wherein the temperature is 20° to 100° C.

20. A process for producing a carbonyl compound which comprises oxidizing a straight or branched chain olefin having 2 to 20 carbon atoms in an alcoholic solvent comprising a monohydric primary or secondary alcohol having 1 to 7 carbon atoms, a polyhydric alcohol having 1 to 7 carbon atoms or a mixture of said monohydric and polyhydric alcohols in the presence of a catalyst system comprising palladium and a polyoxoanion as active components, said polyoxoanion being selected from the group consisting of a heteropolyoxoanion and an isopolyoxoanion, both of which heteropolyoxoanion and isopolyoxoanion comprise a single metal component selected from the group consisting of Mo, W, V, Nb and Ta or a mixed coordination component comprising at least two metals selected from the group consisting of Mo, W, V, Nb and Ta, the oxidation being carried out in the presence of an oxidizing agent selected from the group consisting of pure oxygen and a mixed gas of oxygen with a diluent gas and at a temperature of 0° to 200° C. and at a pressure of atmospheric pressure to 20 kg/cm².

21. The process according to claim 1, wherein the catalyst system consists essentially of a palladium compound and a polyoxoanion compound as active components and the polyoxoanion compound is in an amount of 0.5 to 100 moles per 1 mole of the palladium compound.

22. The process according to claim 20, wherein the solvent is a monohydric alcohol selected from the group consisting of methanol, ethanol, n-propanol, isopropanol, n-butanol, sec-butanol, n-pentanol and n-hexanol.

23. The process according to claim 20, wherein the alcoholic solvent comprises an alcohol having 1 to 7 carbon atoms.

24. The process according to claim 20, wherein the solvent is a polyhydric alcohol selected from the group consisting of ethylene glycol and propylene glycol.

25. The process according to claim 20, wherein the alcoholic solvent further comprises water.

26. The process according to claim 25, wherein an amount of water contained in the alcoholic solvent is not more than 60% by weight.

27. The process according to claim 26, wherein an amount of water contained in the alcoholic solvent is not more than 40% by weight.

28. The process according to claim 20, wherein the catalyst system comprises a palladium compound and a polyoxoanion compound and the polyoxoanion compound is an amount of 0.5 to 100 moles per 1 mole of the palladium compound.

29. The process according to claim 20, wherein the catalyst system comprises of a single compound which comprises both palladium and a polyoxoanion in the molecule.

30. The process according to claim 20, wherein the olefin has 2 to 8 carbon atoms.

31. The process according to claim 20, wherein the olefin has 2 to 4 carbon atoms.

32. The process according to claim 20, wherein the palladium is in the form of a palladium compound selected from the group consisting of palladium sulfate, palladium nitrate, palladium chloride, palladium bromide, palladium acetate, palladium hydroxide, palladium oxide and tetrachloropalladium acid.

33. The process according to claim 32, wherein the polyoxoanion is in the form of a compound with a counter cation, the polyoxoanion being selected from the group consisting of
$[PMo_6 V_6 O_{40}]^{9-}$, $[PMo_4 V_8 O_{40}]^{11-}$,
$[PMo_8 V_4 O_{40}]^{7-}$ $[P_2 W_{12}Mo_5 VO_{62}]^{7-}$,
$[P_2 W_{15}Mo_2 VO_{62}]^{7-}$,
$[Mo_4 V_8 O_{38}]^{8-}$, $[Mo_3 V_3 3O_{19}]^{5-}$,
$[Mo_6 V_2 O_{26}]^{6-}$, $[Mo_6 V_6 O_{36}]^{6-}$,
$[W_7 Mo_3 V_2 O_{36}]^{2-}$ and
$[Mo_8 V_4 O_{36}]^{4-}$.
and the counter cation being selected from the group consisting of $H^+$, $Li^+$, $Na^+$, $K^+$, $Ca^{2+}$, $Mg^{2+}$, $Cu^{2+}$, $Pd^{2+}$, $Fe^{2+}$, $Mn^{2+}$, $Co^{2+}$, onium and ammonium.

34. The process according to claim 33, wherein the polyoxoanion compound is selected from the group consisting of
$H_9 [PMo_6 V_6 O_{40}]$, $H_{11}[PMo_4 V_8 O_{40}]$,
$H_7 [PMo_8 V_4 O_{40}]$, $H_7 [P_2 W_{12}Mo_5 VO_{62}]$, and
$H_7 [P_2 W_{15}Mo_2 VO_{62}]$, 35. The process according to claim 34, wherein the polyoxoanion is in an amount of 1 to 20 moles per mole of the palladium.

36. The process according to claim 35, wherein the solvent consists essentially of an alcohol selected from the group consisting of methanol, ethanol, n-propanol, isopropanol, n-butanol, sec-butanol, n-pentanol, n-hexanol, ethylene glycol and propylene glycol.

37. The process according to claim 36, wherein the alcohol is in an amount of 1 to 10,000 liters per mole of the palladium.

38. The process according to claim 37, wherein the olefin is selected from the group consisting of ethylene, propylene, 1-butene, trans-2-butene, cis-2-butene, 1-pentene, 2-pentene, 1-hexene, 2-hexene, 3-hexene, 4-methyl-1-pentene, 1-heptene and 1-octene and the olefin is in an amount of 10 to 2,000 moles olefin per mole of the palladium.

39. The process according to claim 38, wherein the oxidizing is carried out at a gaseous hourly space velocity of 20 to 1,000 per hour.

40. The process according to claim 39, wherein the temperature is 20° to 100° C.

* * * * *

UNITED STATES PATENT AND TRADEMARK OFFICE
CERTIFICATE OF CORRECTION

PATENT NO. : 5,103,064

DATED : April 7, 1992

INVENTOR(S) : Yoshinori SAITO et al

It is certified that error appears in the above-identified patent and that said Letters Patent is hereby corrected as shown below:

Title page, right column, under the line starting
"4,723,041" insert
--4,550,212    10/1985    Shioyama et al......568/401

FOREIGN PATENT DOCUMENTS 51-117189    Japan......................568/401--

Column 8, line 59 (claim 8), before "comprises" delete "is".

Column 9, line 16, (claim 12), delete "$Co^{2+}$" and insert --$Cu^{2+}$--.

Signed and Sealed this

Twentieth Day of September, 1994

Attest:

BRUCE LEHMAN

*Attesting Officer*    *Commissioner of Patents and Trademarks*